United States Patent
Hori et al.

(10) Patent No.: US 8,558,169 B2
(45) Date of Patent: Oct. 15, 2013

(54) SAMPLE SUBSTRATE FOR LASER DESORPTION IONIZATION-MASS SPECTROMETRY, AND METHOD AND DEVICE BOTH USING THE SAME FOR LASER DESORPTION IONIZATION-MASS SPECTROMETRY

(75) Inventors: Masaru Hori, Nagoya (JP); Hiroaki Sato, Tsukuba (JP); Yasutake Toyoshima, Tsukuba (JP); Mineo Hiramatsu, Nagoya (JP)

(73) Assignee: Masaru Hori, Nagoya-Shi, Aichi (JP)

( * ) Notice: Subject to any disclaimer, the term of this patent is extended or adjusted under 35 U.S.C. 154(b) by 0 days.

(21) Appl. No.: 13/388,970

(22) PCT Filed: Jul. 29, 2010

(86) PCT No.: PCT/JP2010/004806
§ 371 (c)(1),
(2), (4) Date: Mar. 7, 2012

(87) PCT Pub. No.: WO2011/016204
PCT Pub. Date: Feb. 10, 2011

(65) Prior Publication Data
US 2012/0175515 A1    Jul. 12, 2012

(30) Foreign Application Priority Data
Aug. 6, 2009 (JP) ................................. 2009-183797

(51) Int. Cl.
*H01J 49/00* (2006.01)
(52) U.S. Cl.
USPC ............................ 250/288; 250/281; 250/282
(58) Field of Classification Search
None
See application file for complete search history.

(56) References Cited

U.S. PATENT DOCUMENTS

2005/0277201 A1 * 12/2005 Sivarajan et al. ............. 436/173
2006/0255262 A1   11/2006 Sato et al.
2008/0290270 A1 * 11/2008 Joyce et al. .................... 250/288

FOREIGN PATENT DOCUMENTS

JP  2006-201042 A    8/2006
JP  2006-329977 A   12/2006

(Continued)

OTHER PUBLICATIONS

J. Sunner, E. Dratz, Y.-C. Chen., "Graphite Surface-Assisted Laser Desorption/Ionization Time-of-Flight Mass Spectrometry of Peptides and Proteins from Liquid Solutions", Anal. Chem. 1995: 67: 4335-4342.

(Continued)

*Primary Examiner* — Andrew Smyth
(74) *Attorney, Agent, or Firm* — McGinn Intellectual Property Law Group, PLLC

(57) ABSTRACT

An object of the present invention is to provide a sample substrate for laser desorption ionization mass spectrometry for LDI-MS which substrate enables mass spectrometric analysis of a sample correctly at high sensitivity without generating interference peaks upon irradiation of the sample to laser light and uniform application of the sample onto a base. Another object of the invention is to provide a mass spectrometer (device) employing the sample substrate.

In the sample substrate for laser desorption ionization mass spectrometry, the sample substrate is formed of a base and carbon nanowalls having wall surfaces onto which a sample to undergo mass spectrometry is applied, wherein the carbon nanowalls are formed on the base so as to stand on the base. The surfaces of carbon nanowalls serve as an ionization medium and hydrophilized. By use of the sample substrate, mass spectrometry of a sample having a wide range (high to low) molecular weight can be reliably performed at high precision and sensitivity.

18 Claims, 7 Drawing Sheets

(56) References Cited

FOREIGN PATENT DOCUMENTS

| | | |
|---|---|---|
| JP | 2009-81054 A | 4/2009 |
| WO | WO 2007/097023 A1 | 8/2007 |

OTHER PUBLICATIONS

International Search Report (ISR) (PCT Form PCT/ISA/210) dated Aug. 24, 2010, in PCT/JP2010/004806.

Tang Ho-Wai, et al., "Ion Desorption Efficiency and Internal Energy Transfer in Carbon-Based Surface-Assisted Laser Desorption/Ionization Mass Spectrometry: Desorption Mechanism(s) and the Design of Saldi Substrates", Anal. Chem., vol. 81, No. 12, Jun. 15, 2009, p. 4720-4729.

Mineo Hiramatsu, et al., "Sho Tokushu Plasma Process ni yoru Carbon Nano Tube Haiko Seicho no Genjo to Kadai 5.RF Plasma CVD ni yoru Carbon Nano Wall no. Haiko Seicho", J. Plasma Lysuib Res., vol. 81, No. 9, 2005, pp. 669 to 673.

Ryuichi Arakawa, et al., "Nano Kozo o Riyo shita Hyomen Shien Laser Datsun Ion-ka Shisturyo Bunsekiho", Bunseki, No. 5, May 5, 2008, pp. 230 to 234.

Japanese Office Action dated Apr. 16, 2013 with partial English translation thereof.

\* cited by examiner

FIG. 5 Mass spectra of 4,4'-(α,α-dimethylbenzyl)diphenylamine measured in Example 1 and Comparative Example 1

Mass spectrum of Irganox 1035 measured in Example 2

Mass spectrum of Triton X-100 measured in Example 3

Mass spectrum of angiotensin-I measured in Example 4

Mass spectrum of myoglobin measured in Example 5

Mass spectrum of β-cyclodextrin measured in Example 6

SAMPLE SUBSTRATE FOR LASER DESORPTION IONIZATION-MASS SPECTROMETRY, AND METHOD AND DEVICE BOTH USING THE SAME FOR LASER DESORPTION IONIZATION-MASS SPECTROMETRY

TECHNICAL FIELD

The present invention relates to a sample substrate for laser desorption ionization mass spectrometry, and to a method and device for laser desorption ionization mass spectrometry employing the sample substrate. More particularly, the invention relates to such a sample substrate which employs no matrix for assisting soft ionization and to an analytical method and an analysis device employing the sample substrate.

BACKGROUND ART

Hitherto, the molecular weight of a bio-substance (e.g., protein, peptide, saccharide, or oligonucleotide), a polymer, or a synthetic polymer has been known to be correctly determined through laser desorption ionization mass spectrometry (LDI-MS) by means of a measurement device therefor.

In the analytical method, individual molecules of the sample are required to be ionized through laser radiation without decomposing the molecules. In a procedure typically employed to avoid decomposition of sample molecules, a sample is applied onto a medium which absorbs laser light, or a mixture of a sample and a medium which absorbs laser light is fed to a spectrometer. This ionization technique without causing decomposition of the sample is called "soft LDI-MS." One known technique among soft LDI-MS techniques is a matrix-assisted laser desorption ionization mass spectrometry (MALDI-MS). In mass spectrometry, a sample is fragmented by means of a mass-separation section of a TOF (time-of-flight) type, a quadrupole type, an ion-trap type, a sector type, a Fourier-transformation type, or a combination thereof, the thus-separated fragment ions are detected by means of a detector, and the mass numbers of the ions are determined. Among such techniques, a method employing a time-of-flight mass separation section is frequently employed, since no particular limitation is imposed on the principally measureable mass range. In matrix-assisted laser desorption ionization mass spectrometry, a variety of matrices are used.

Meanwhile, in MALDI-MS, a low-molecular-weight organic compound is used as an ionizing agent, and interfering ions are generated from the agent. The thus-generated interfering ions have molecular weights almost equivalent to the molecular weight of the organic compound (mass number: ≤500), and these interfering ions form clusters having total molecular weights of $10^3$ or higher (as mass number). All these ions mask target ions to be detected, generally making mass spectrometry of a sample molecule of interest difficult. In addition, in MALDI-MS, the type of a matrix agent suitable for ionization varies depending on the type of sample molecule. Therefore, an analysis sample must be prepared with an appropriately selected matrix agent, and such selection is carried out on a trial and error basis, which is inconvenient. In order to overcome the drawback, there is proposed soft LDI-MS employing an inorganic compound in micropowder form serving as an ionizing agent.

As disclosed in Patent Documents 1 and 2 (in "Background Art" section), examples of the micropowder-form inorganic compound include cobalt micropowder, titanium oxide micropowder, graphite powder, carbon nanotubes, and solid carbon black (mean particle size: ≤100 nm, PVC blackness: ≤50). Also known is a technique for suppressing locational variation in sensitivity and resolution in which a support substrate having a carbon-containing surface layer is used, to thereby uniformly and minutely crystallize sample molecules. In the micropowder method, since a suspension of the liquid sample and micropowder is applied onto a sample substrate for mass spectrometry, difficulty is encountered in uniformly applying the sample. Particularly in the case of high-sensitivity mass spectrometry, failure to attain uniform application is generally problematic. In addition, an ionization medium is scattered in an ion source chamber through laser light radiation, resulting in problematic contamination.

In order to overcome the above problem, there is proposed a soft LDI-MS technique employing a porous silicon substrate as a sample substrate, the method being called a desorption/ionization-mass spectrometry on porous silicon (DIOS-MS). In DIOS-MS, a sample solution is applied onto the surface of a porous silicon substrate having nano-order micropores and dried. The thus-treated substrate is placed in an ion source in the mass spectrometer, and subjected to the same subsequent procedure as performed in MALDI-MS. The surface of the sample is irradiated with laser light, whereby mass spectrometry is performed. Although the principle of ionization in DIOS-MS has not been elucidated in detail, one conceivable mechanism for ionizing a sample is as follows. The silicon nano-structure is rapidly heated via high-efficiency absorption of laser light, whereby sample molecules instantaneously dissociate. Also, components bounded to or adsorbed on porous silicon are ionized, to thereby transfer electric charge to the sample molecules.

There have also been proposed other sample substrates. Examples include a silicon nano-wire substrate formed of a silicon substrate on which silicon nano-wire has been grown on gold microparticles deposited on the silicon substrate, a plastic substrate having a grooved surface, a substrate coated with metal membrane, an etched silicon substrate, and a chip-like substrate employing a sponge-form substance.

DIOS-MS is an advantageous technique in that a sample substrate itself is employed as an ionization medium, to thereby facilitate uniform application of a sample and prevent problematic generation of interference peaks which would otherwise occurs in MALDI-MS. However, the ionization efficiency varies considerably depending on the conditions under which porous silicon has been formed, and great difficulty is encountered in production of sample substrates having the same porous structure at high reproducibility. Thus, at present, DIOS-MS cannot necessarily be employed as a reliable mass spectrometric technique. Furthermore, since a large portion of the applied sample are incorporated into the porous structure, most of the sample molecules are not ionized and remain in the porous structure. Such unionized molecules interfere with high-sensitivity measurement and make washing of the sample substrate after measurement difficult. Failure in washing causes prevention of generation of peaks attributed to a precedent sample. Thus, DIOS-MS is not necessarily a suitable technique for repeated sample measurement.

In the nano-wire method, gold microparticles serving as a nano-wire material are mechanically bonded to the silicon substrate in an unstable state. Therefore, the nano-wire-gold microparticle structure is prone to be broken by laser light irradiation in measurement or in a sample substrate washing step performed after measurement. Thus, the nano-wire method is not necessarily a suitable technique for repeated sample measurement.

Under such circumstances, the present inventors previously developed techniques disclosed in Patent Documents 1 and 2. The technique disclosed in Patent Document 1 employs, as an ionization medium for absorbing laser light, a pyroelectric (e.g., ferroelectric) crystal substrate having a flat surface. In this technique, pyroelectric crystals are instantaneously polarized by photoenergy of laser light, and sample molecules are ionized by utilizing surface charge or electric field generated by the polarization. One problem involved in the technique is a small specific surface area of the flat substrate onto which a sample is applied, resulting in low sensitivity. Accordingly, in order to enhance sensitivity, the present inventors developed the technique disclosed in Patent Document 2. In the technique disclosed in Patent Document 2, sensitivity is enhanced by forming a large number of fine protruded dots (i.e., quantum dots having a diameter of 20 nm to 100 nm) made of semiconductor on the surface of a flat semiconductor substrate, to thereby increase the specific surface area of the substrate. Since the substrate employs quantum dots, washing of the substrate is easier as compared with the aforementioned porous silicon substrate.

Meanwhile, graphite has a laminar structure in which carbon atoms are hexagonally bonded together and each plane is formed of the hexagons arranged in a plane. The π-electron orbitals of the carbon atoms extend in a direction normal to the plane direction, whereby an unordinary electric field is provided near the graphite surface. Graphite is also known to efficiently absorb laser light employed in laser desorption ionization mass spectrometry. Thus, studies have been conducted on graphite powder as a matrix employed in LDI-MS (Non-Patent Document 1). However, as described in the sections of "Background Art" and "Examples" in Patent Document 3, when graphite powder which has been subjected to no further treatment is employed as a matrix, graphite scatters to generate interference peaks, and the scattered graphite contaminates the ion source chamber, which is considerably problematic. Due to conductivity, graphite as a contaminant provides electric discharge upon application of high voltage thereto for ion acceleration by the ion source chamber, and the electric discharge may give severe damage to relevant devices. Therefore, an LDI-MS technique employing graphite powder is applied to a limited range of research. One alternative substrate for overcoming the drawback is produced by dispersing graphite powder in water-ethanol solvent, to thereby form thin film, and thermally fixing the thin film onto OHP film (Patent Document 3). Although scattering of graphite is prevented in the production procedure, the particle size, amount, and film thickness and graphite powder forming the graphite thin film cannot be controlled precisely or uniformly.

At present, there has never been provided a sample substrate for laser desorption ionization mass spectrometry which substrate can be used to carry samples having a wide range of molecular weights, can gain sufficient sensitivity without noise, and has locational uniformity in sensitivity. Therefore, there is keen demand for a sample substrate which enables uniform application of a sample solution thereto, which does not generate interference peaks upon irradiation of the sample-coated substrate surface with laser light, which can be easily washed after measurement, which can be applied to analysis of various samples, and which attains high-sensitivity measurement. In addition, there is demand for realization of the method and device in laser desorption ionization mass spectrometry employing the substrate having such characteristics to prevent generation of interference peaks, with respect to mass spectrometry of various substances.

PRIOR ART DOCUMENTS

Patent Documents
Patent Document 1: Japanese Patent Application Laid-Open (kokai) No. 2006-201042
Patent Document 2: Japanese Patent Application Laid-Open (kokai) No. 2006-329977
Patent Document 3: Japanese Patent Application Laid-Open (kokai) No. 2009-81054
Non-Patent Documents
Non-Patent Document 1: J. Sunner, E. Dratz, Y.-C. Chen., Anal. Chem. 1995: 67: 4335-4342

DISCLOSURE OF THE INVENTION

Problems to be Solved by the Invention

An object of the present invention is to provide a sample substrate for laser desorption ionization mass spectrometry which enables mass spectrometric analysis of a variety of samples having a wide range of molecular weight (biosamples and synthetic organic compounds) correctly at high sensitivity without generating interference peaks upon irradiation of the samples with laser light.

Another object of the invention is to provide a sample substrate for soft LDI-MS, which enables uniform application of a sample in sample preparation, which attains high detection sensitivity, and which exhibits small locational variation in detection sensitivity. Still another object is to provide a measurement method and device employing the sample substrate.

Means for Solving the Problems

In a first aspect of the present invention, there is provided a sample substrate for laser desorption ionization mass spectrometry, characterized in that the sample substrate comprises a base and carbon nanowalls having wall surfaces onto which a sample to undergo mass spectrometry is applied, wherein the carbon nanowalls are formed on the base so as to stand on the base.

A second aspect of the invention is directed to a specific embodiment of the sample substrate for laser desorption ionization mass spectrometry according to the first aspect, wherein the surfaces of the carbon nanowalls serve as a medium for ionization of the sample.

A third aspect of the invention is directed to a specific embodiment of the sample substrate for laser desorption ionization mass spectrometry according to the first or second aspect, wherein the surfaces of the carbon nanowalls have been hydrophilized.

In a fourth aspect of the present invention, there is provided a method for performing laser desorption ionization mass spectrometry, characterized in that the method comprises employing a sample substrate for laser desorption ionization mass spectrometry as recited in any one of the first to third aspects.

In a fifth aspect of the present invention, there is provided a device for performing laser desorption ionization mass spectrometry, characterized in that the device is configured to receive therein a sample substrate for laser desorption ionization mass spectrometry as recited in any one of the first to third aspects.

In a sixth aspect of the present invention, there is provided a sample for laser desorption ionization mass spectrometry, characterized in that the sample is produced by preparing a solution of a sample, applying the sample solution onto a sample substrate for laser desorption ionization mass spectrometry as recited in any one of the first to third aspects, and drying.

The present inventors have conducted extensive studies in order to develop a high-performance ionization substrate, and have found that increasing the specific surface of the substrate is important for attaining high sensitivity, and that carbon nanowalls, having high a high aspect ratio and a considerably large specific surface area, are effectively employed in a substrate onto which a sample for mass spectrometry is applied. As a result, the present inventors have accomplished the sample substrate of the present invention for laser desorption ionization mass spectrometry, the sample substrate comprising a base, and carbon nanowalls formed on the base so as to stand on the base, which enables uniform application of a sample solution thereto, which does not generate interference peaks upon irradiation of the sample-coated substrate surface with laser light, and which can be easily washed after measurement.

In other words, the inventors have found that, by use, as an ionization medium, of a base having a carbon nanowall structure (i.e., a structure which is high-efficiency laser light absorbent) formed on the surface thereof, generation of interference peaks upon irradiation of the sample substrate with laser light can be prevented, whereby soft LDI-MS can be performed with respect to a variety of samples having a wide range of molecular weight correctly at high sensitivity with only a small locational variation in detection sensitivity.

In the present invention, a carbon nanowall structure is suitable for an ionization element, since carbon nanowalls can distribute absorbed laser light energy to samples. No particular limitation is imposed on the material of the base, so long as the base allows carbon nanowalls to grow in a direction vertical to the main surface of the base. Since the sample substrate of the present invention for laser desorption ionization mass spectrometry is formed of an inorganic compound, generation of interference peaks attributed to the ionization medium can be avoided in soft LDI-MS.

According to the present invention, a sample substrate can be produced in a very simple manner without performing micro-processing such as etching, and no variation is observed in aspect ratio or area density of the formed carbon nanowalls. Therefore, in the case where a large number of samples are analyzed, all the samples can be analyzed at the same sensitivity.

In addition, the carbon-carbon bonds in carbon nanowalls and the bonding between carbon nanowalls and the base are very strong. Therefore, when carbon nanowalls or the base is irradiated with laser light, generation of interference peaks, which would otherwise be caused by breaking of the microstructure via absorption of laser light, there can be prevented release of small masses of carbon and a substance forming the substrate, as well as ionization of the small masses.

That is, according to the present invention, the relationship: (dissociation energy of analysis sample)<(laser energy absorbed by substrate)<(interatomic bond energy for forming carbon nanowalls) can be satisfied. As a result, in the present invention, the protruded structure formed on the smooth surface is chemically bonded to the substrate at high bonding strength. Therefore, the protruded structure of carbon nanowalls is not broken or dissociated from the substrate by laser radiation. Thus, noise-free soft ionization can be realized.

In soft LDI-MS, a high voltage of about 20,000 V is applied to a sample substrate for accelerating generated ions. Therefore, carbon nanowalls—ionizing material—must be set in a conductive sample substrate holder. If fixation is performed by use of fixation means such as double-sided tape or a plastic part, a gas component released from the fixation means may cause lowering of the degree of vacuum and contamination of the inside of the device. When fixation is performed by means of a metal jig, the sample substrate may be broken or damaged. In contrast, according to the present invention, an element (conductive carbon nanowalls) and a sample substrate holder (conductive member) are integrated. Thus, a mass spectrometer employing such an integrated sample substrate can be simplified, to thereby prevent lowering the degree of vacuum and contamination of the inside of the device. That is, a high-performance mass spectrometer can be provided.

Effects of the Invention

By use of the sample substrate according to the present invention for laser desorption ionization mass spectrometry, interference peaks attributed to an ionizing agent during irradiation of the substrate with laser light can be prevented, whereby correct measurement can be attained. In addition, through employment of an ionization medium formed of a carbon nanowall structure standing upright from the substrate surface, a considerably large specific surface area can be provided, whereby measurement sensitivity can be enhanced.

Since the ionization substrate of the present invention is formed from an inorganic material, and the surface of the substrate onto which a measurement sample is applied is chemically stable, the substrate of the invention has no surface instability, which a microporous ionization substrate has, whereby reproducibility of measurements can be ensured.

The substrate of the present invention can be produced through a routine dry process such as plasma deposition, and a wet process such as etching with hydrofluoric acid, which is employed for producing porous silicon, is not required. Thus, mass production of the substrate of the invention can be readily realized.

Furthermore, a carbon nanowall structure in which wide carbon walls are formed at a uniform in-plane density so as to stand from the substrate with nanometer-order spacing intervals can be readily produced. Thus, locational variation in sensitivity can be avoided.

BRIEF DESCRIPTION OF THE DRAWINGS

FIG. 2 FIGS. 2(a), 2(b), and 2(c) are SEM images of cross sections of carbon nanowalls produced through production methods under given conditions, and FIGS. 2(d), 2(e), and 2(f) are SEM images of the top surfaces of the same carbon nanowalls.

DESCRIPTION OF REFERENCE NUMERALS

Figure 1:
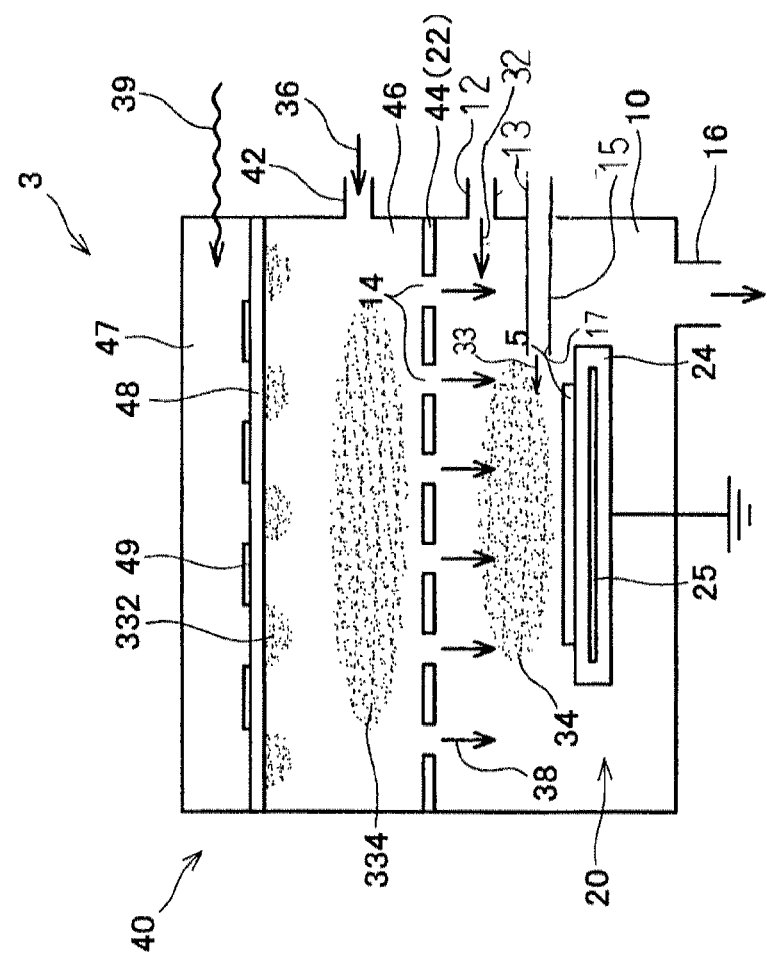
FIG. 1 A schematic representation of a production apparatus for carrying out a production method according to a specific embodiment of the present invention.

1 ... Carbon nanowall production apparatus
10 ... Reaction chamber
12 ... Raw material gas inlet
13 ... Oxygen gas inlet
14 ... Radical inlet
20 ... Plasma discharge means
22 ... First electrode
24 ... Second electrode
5, 50 ... Sample substrate for mass spectrometry
55 ... Carbon nanowalls
61 ... Sample holder
63 ... Laser device
64 ... Detector

MODES FOR CARRYING OUT THE INVENTION

Hereinafter, the method for producing a sample substrate for laser desorption ionization mass spectrometry will be described in detail.

The present inventors have found that carbon nanowalls of high quality can be grown on a substrate by adding oxygen plasma to a plasma atmosphere containing carbon and fluorine. The raw material substance employed is preferably at least one of member selected from among $C_2F_6$, $CF_4$, and $CHF_3$.

Preferably, hydrogen radicals are generated at a site different from the plasma atmosphere for growing carbon nanowalls on a substrate, and the hydrogen radicals are injected into the plasma atmosphere. According to such a production method, one or more of conditions (e.g., the composition and feed rate of the radicals injected into the plasma atmosphere) may be controlled independently of or in conjunction with one or more of other production conditions. That is, the production method provides higher flexibility in controlling production conditions, as compared with the case where no radicals are injected from outside the plasma atmosphere. This is advantageous from the viewpoint of production of carbon nanowalls exhibiting properties of interest (e.g., the thickness, height, density on the substrate, smoothness, and surface area of formed nanowalls) and/or characteristics of interest (e.g., electrical characteristics such as field emission characteristics).

As used herein, the term "carbon nanowall(s)" is used to refer to a carbon nano-scale structure (hereinafter may be referred to as a "carbon nanostructure") which extends two-dimensionally. Carbon nanowalls are formed of graphene sheets which extend two-dimensionally and which are provided so as to stand on a surface of a base, and each nanowall is formed of a single layer or multiple layers. As used herein, the expression "extend two-dimensionally" refers to the case where the lengths of a carbon nanowall in longitudinal and lateral directions are sufficiently greater than the thickness (width) thereof. Such a carbon nanowall may be formed of multiple layers, a single layer, or a pair of layers (with a space provided therebetween). The upper surfaces of carbon nanowalls may be covered so that cavities are provided therebetween. For example, carbon nanowalls have a thickness of about 0.05 to about 30 nm, and a longitudinal or lateral length of about 100 nm to about 10 μm. In general, a carbon nanowall is expressed as "extending two-dimensionally," since the lengths of the carbon nanowall in longitudinal and lateral directions are much greater than the width thereof, and thus can be controlled.

Typically, carbon nanowalls produced through the aforementioned production method are of a carbon nanostructure formed of upright walls extending from the surface of a base in generally the same direction. As used herein, the term "plasma atmosphere" refers to an atmosphere in which at least a portion of a substance forming the atmosphere is in an ionized state (in a state of plasma; i.e., in a state of a mixture containing, for example, charged particles such as atomic ions, molecular ions, or electrons, and neutral particles such as atomic radicals or molecular radicals).

In a preferred mode of the production method disclosed herein, the plasma atmosphere is provided by forming a plasma of a raw material(s), hydrogen plasma, and oxygen plasma in the reaction chamber. Alternatively, a plasma of a raw material(s), hydrogen plasma, and oxygen plasma may be formed outside of the reaction chamber, and the thus-formed plasmas may be introduced into the reaction chamber, to thereby form the plasma atmosphere therein. Still alternatively, only a plasma of a raw material(s) may be formed in the reaction chamber; oxygen radicals and hydrogen radicals may be generated in a chamber different from the reaction chamber; and these radicals may be injected into the plasma atmosphere in the reaction chamber. Yet alternatively, a plasma of a raw material(s) and oxygen plasma may be formed in the reaction chamber; only hydrogen radicals may be generated in a chamber different from the reaction chamber; and the hydrogen radicals may be injected into the plasma atmosphere in the reaction chamber. Yet alternatively, a plasma of a raw material(s) and hydrogen plasma may be formed in the reaction chamber; only oxygen radicals may be generated in a chamber different from the reaction chamber; and the oxygen radicals may be injected into the plasma atmosphere in the reaction chamber.

In a preferred method for generating radicals from a radical source substance, the radical source substance is irradiated with an electromagnetic wave. Examples of the electromagnetic wave which may be employed in such a method include microwaves and high-frequency waves (UHF waves, VHF waves, and RF waves). Irradiation of a VHF wave or an RF wave is particularly preferred. According to such a method, the degree of decomposition of a radical source substance (i.e., the amount of radicals generated) can be readily controlled by varying, for example, frequency and/or input electric power. Therefore, such a method is advantageous in that conditions for production of carbon nanowalls (e.g., the amount of radicals supplied into the plasma atmosphere) are readily controlled.

As has been well known, the term "microwave" refers to an electromagnetic wave having a frequency of about 1 GHz or more; "UHF wave" refers to an electromagnetic wave having a frequency of about 300 to about 3,000 MHz; "VHF wave" refers to an electromagnetic wave having a frequency of about 30 to about 300 MHz; and "RF wave" refers to an electromagnetic wave having a frequency of about 3 to about 30 MHz. In another preferred method for generating radicals from a radical source substance, DC voltage is applied to the radical source substance. Generation of radicals from a radical source substance may also be carried out through, for example, a method in which the radical source substance is irradiated with light (e.g., visible light or UV rays), a method in which the radical source substance is irradiated with an electron beam, or a method in which the radical source substance is heated. Alternatively, generation of radicals from a radical source substance may be carried out by bringing the radical source substance into contact with a heated catalytic-metal-containing member (i.e., through heat and catalytic action). The aforementioned catalytic metal may be one or more species selected from among, for example, Pt, Pd, W, Mo, and Ni.

Radicals injected into the plasma atmosphere preferably contain at least hydrogen radicals (i.e., atomic hydrogen, hereinafter may be referred to as "H radicals"), and oxygen radicals (i.e., atomic oxygen, hereinafter may be referred to as "O radicals"). Preferably, H radicals are generated through decomposition of a radical source substance containing at least hydrogen as its constituent element, and the thus-generated H radicals are injected into the plasma atmosphere. Such a radical source substance is particularly preferably hydrogen gas ($H_2$).

The raw material substance may be selected from a variety of substances each containing at least carbon as a constituent element. Only a single raw material substance may be employed, or two or more raw material substances may be employed in any proportions. Examples of preferred raw material substances include substances containing at least carbon and hydrogen as constituent elements (e.g., hydrocarbon). Examples of other preferred raw material substances include substances containing at least carbon and fluorine as constituent elements (e.g., fluorocarbon).

The raw material substance may also be a substance material containing carbon, hydrogen, and fluorine as essential constituent elements (e.g., fluorohydrocarbon). As described hereinbelow, particularly when a substance containing carbon and fluorine as constituent elements (e.g., $C_2F_6$ or $CF_4$) is employed, carbon nanowalls having good shape are formed. Also, when a substance containing carbon, hydrogen, and fluorine as constituent elements (e.g., $CHF_3$) is employed, carbon nanowalls having good shape are formed.

The present inventors have found that the shape, interwall spacing, thickness, or size of carbon nanowalls formed can be controlled through modifying the ratio of the flow rate of $H_2$ gas (i.e., radical source substance) to that of a raw material gas, the ratio being the relative amount of H radicals injected into a reaction zone. Therefore, properties of formed carbon nanowalls can be controlled by regulating the feed rate of the radicals into the reaction zone.

In a preferred mode of the production method disclosed herein, at least one of the conditions for producing carbon nanowalls is controlled on the basis of the amount of at least one type of radical concentration of the atmosphere of the reaction chamber (e.g., at least one radical concentrations selected from among carbon radical concentration, hydrogen radical concentration, fluorine radical concentration, oxygen radical concentration, and fluorocarbon radical concentration). Examples of the production condition which may be controlled on the basis of such a radical concentration include the feed rate of a raw material substance(s), conditions required for forming a plasma of a raw material substance(s) (severity of plasma formation conditions), and the amount of radicals (typically, H radicals) injected. Preferably, such production conditions are controlled on the basis of the feedback results of the aforementioned radical concentration. According to the production method, carbon nanowalls exhibiting properties and/or characteristics of interest can be more effectively produced.

According to the production method, carbon nanowalls are effectively formed in the absence of a metal catalyst on the surface of the base. Needless to say, carbon nanowalls may be formed in the presence of a metal catalyst.

Thus, since oxygen plasma is added to a plasma atmosphere containing carbon, fluorine, and hydrogen, carbon nanowalls having good crystallinity can be grown on a substrate. Particularly, the method of the present invention can produce carbon nanowalls which have no branching in a direction of height and extend smoothly. The aspect ratio (height of wall/width of wall) of carbon nanowall reaches 200 or higher.

The raw material substance used in the production of carbon nanowalls may be selected from among substances containing at least carbon as a constituent element. The element which can constitute such a raw material together with carbon is one or more elements selected from among, for example, hydrogen, fluorine, chlorine, bromine, nitrogen, and oxygen. Examples of preferred raw material substances include a substance virtually consisting of carbon and hydrogen, a substance virtually consisting of carbon and fluorine, and a substance virtually consisting of carbon, hydrogen, and fluorine. For example, a fluorocarbon (e.g., $C_2F_6$) or a fluorohydrocarbon (e.g., $CHF_3$) is preferably employed. Such a raw material substance having a linear, branched, or cyclic molecular structure may be employed. Generally, a raw material substance which is in a gaseous state at ambient temperature and ambient pressure (i.e., a raw material gas) is preferably employed. Only a single raw material substance may be employed, or two or more raw material substance may be employed in any proportions. The type (composition) of a raw material substance(s) employed may be unchanged throughout production stages (e.g., a growth process) of carbon nanowalls, or may be changed depending on the production stages. The type (composition) of a raw material substance(s) employed, the method for supplying the raw material substance(s), or other conditions may be appropriately determined in consideration of properties (e.g., wall thickness) and/or characteristics (e.g., electrical characteristics) of a carbon nanostructure of interest.

The radical source substance employed is preferably a material containing at least hydrogen as its constituent element. Preferably, a radical source substance which is in a gaseous state at ambient temperature and ambient pressure (i.e., a radical source gas) is employed. Hydrogen gas ($H_2$) is a particularly preferred radical source substance. The radical source substance employed may be a material which can generate H radicals through decomposition (e.g., a hydrocarbon such as $CH_4$). Only a single radical source substance may be employed, or two or more radical source substances may be employed in any proportions.

In the production method disclosed herein, radicals are injected into an atmosphere containing a plasma of a raw material substance(s) and oxygen plasma. Thus, the raw material plasma, oxygen plasma, and radicals (typically, H radicals) are mixed together. Specifically, radicals (H radicals) are present at high concentration in the raw material plasma atmosphere. Oxygen radicals and hydrogen radicals may be injected into the raw material plasma atmosphere. Carbon nanowalls are formed (grown) on a base through deposition of carbon thereon from the atmosphere containing the raw material plasma, oxygen plasma, and radicals. Examples of the base which may be employed include a base in which at least a region on which carbon nanowalls are formed is made of Si, $SiO_2$, $Si_3N_4$, GaAs, $Al_2O_3$, or a similar material. The entirety of the base employed may be made of any of the aforementioned materials. According to the aforementioned production method, carbon nanowalls can be formed directly on a surface of the aforementioned base without using a catalyst such as nickel-iron. However, a catalyst such as Ni, Fe, Co, Pd, or Pt (typically, a transition metal catalyst) may be employed. For example, a thin film (e.g., a film having a thickness of about 1 to about 10 nm) of any of the aforementioned catalysts may be formed on a surface of the aforementioned base, and carbon nanowalls may be formed on the catalyst thin film. No particular limitation is imposed on the outer shape of the base employed. Typically, a plate form base (substrate) is employed.

FIG. 1 shows a configuration of an apparatus for producing carbon nanowalls. As shown in FIG. 1, an apparatus 3 according to the embodiment includes radical supply means 40, and the radical supply means 40 includes a plasma formation chamber 46 provided above a reaction chamber 10. The plasma formation chamber 46 is separated from the reaction chamber 10 by a partition 44 which is provided so as to face the surface of the substrate 5 on which carbon nanowalls are formed. A waveguide 47 for guiding microwaves 39 is provided above the plasma formation chamber 46. The microwaves are introduced into the plasma formation chamber 46 through quartz windows 48 by means of slot antennas 49, to thereby form a high-density plasma 332. The plasma 332 is caused to diffuse in the plasma formation chamber 46 (plasma 334), whereby radicals 38 are generated. Bias voltage may be appropriately applied to the partition 44. For example, bias voltage may be applied between the partition 44 and the plasma 334 in the plasma formation chamber 46, or between the partition 44 and a plasma atmosphere 34 in the reaction chamber 10. The direction of bias voltage may be appropriately varied. Preferably, the apparatus is configured so that negative bias voltage can be applied to the partition 44.

Ions generated from the plasma 334 are electrically neutralized at the partition 44, to thereby generate the radicals 38. In this case, percent neutralization may be appropriately increased through application of an electric field to the partition 44. Energy may be applied to the neutral radicals. Numerous through-holes are distributed in the partition 44. The radicals 38 are introduced through these through-holes (serving as numerous radical inlets 14) into the reaction chamber 10 and diffused as is therein, and then the radicals 38 are injected into the plasma atmosphere 34. As shown in FIG. 1, the inlets 14 are provided in a direction parallel to the top surface of the substrate 5 (i.e., the surface on which carbon nanowalls are formed).

With this configuration of the apparatus 3, the radicals 38 can be more uniformly introduced to a wider region in the reaction chamber 10. Therefore, carbon nanowalls can be effectively formed on a wider region (area) of the substrate 5. In addition, carbon nanowalls having more uniform structural features (properties, characteristics, etc.) can be formed at any portions of the substrate surface. According to the embodiment, one or more of these effects can be achieved.

The partition 44 may be coated with a material exhibiting high catalytic performance (e.g., Pt), or may be made of such a material itself. When an electric field is applied between the partition 44 having such a structure and the plasma atmosphere 34 (typically, negative bias voltage is applied to the partition 44), ions contained in the plasma atmosphere 34 are accelerated, and the partition 44 is sputtered by the ions, whereby atoms (e.g., Pt) or clusters exhibiting catalytic performance can be injected into the plasma atmosphere 34.

In a carbon nanowall formation process, employed are the radicals 38 (typically, H radicals) injected from the plasma formation chamber 46, radicals and/or ions containing at least carbon, the radicals and/or ions being generated in the plasma atmosphere 34, and atoms or clusters exhibiting catalytic performance which are generated through the aforementioned sputtering of the partition 44 and injected into the plasma atmosphere 34. Thus, atoms, clusters, or fine particles exhibiting catalytic performance may be deposited in the interiors and/or on the surfaces of the thus-formed carbon nanowalls. The carbon nanowalls containing such atoms, clusters, or fine particles are applicable to, for example, a material for an electrode of a fuel cell, since the carbon nanowalls can exhibit high catalytic performance.

Plasma discharge means 20 is configured so as to serve as a parallel plate-type capacitively coupled plasma (CCP) formation mechanism. The plasma discharge means 20 includes a first electrode 22 and a second electrode 24, each of which has a generally disk shape. These electrodes 22 and 24 are disposed in the reaction chamber 10 so as to be generally parallel to each other. Typically, the first electrode 22 is disposed above the second electrode 24. The first electrode (cathode) 22 is connected to a power supply (not illustrated) via a matching network (not illustrated). The power supply and the matching network can generate at least one of RF waves (e.g., 13.56 MHz), UHF waves (e.g., 500 MHz), VHF waves (e.g., 27 MHz, 40 MHz, 60 MHz, 100 MHz, and 150 MHz), and microwaves (e.g., 2.45 GHz). The power supply and the matching network are configured so that at least RF waves can be generated.

The second electrode 24 is disposed in the reaction chamber 10 so as to be away from the first electrode 22. The distance between the electrodes 22 and 24 may be, for example, about 0.5 to about 10 cm. In the embodiment, the distance is about 5 cm. The second electrode 24 is grounded. For production of carbon nanowalls, the substrate (base) 5 is placed on the second electrode 24. For example, the substrate 5 is placed on the top surface of the second electrode 24 so that a surface of the base 5 on which carbon nanowalls are produced is exposed (i.e., faced to the first electrode 22). The second electrode 24 includes therein a heater 25 (e.g., a carbon heater) serving as base temperature control means. Optionally, the temperature of the substrate 5 may be controlled by operating the heater 25.

The reaction chamber 10 is provided with a raw material inlet 12 through which a raw material substance (raw material gas) can be supplied from a supply source (not illustrated). In a preferred mode, the inlet 12 and an oxygen inlet 13 are provided so that a raw material gas and oxygen gas can be supplied between the first electrode (upper electrode) 22 and the second electrode (lower electrode) 24. A supply tube 15 extending from the oxygen inlet 13 in the reaction chamber 10 to the vicinity of the substrate 5 is provided so as to be parallel to the substrate 5. The supply tube 15 has a discharge outlet 17 provided in the vicinity of the substrate 5. The inlets 14 are provided so that radicals can be introduced between the first electrode 22 and the second electrode 24. The reaction chamber 10 also includes a discharge outlet 16. The discharge outlet 16 is connected to, for example, a vacuum pump (not illustrated) serving as pressure control means (pressure reducing means) for controlling the pressure in the reaction chamber 10. In a preferred mode, the discharge outlet 16 is provided below the second electrode 24.

Microwaves (e.g., 2.45 GHz) are introduced directly into the radical supply means 40, and hydrogen plasma is formed from supplied hydrogen gas in the plasma formation chamber 46, whereby H radicals are generated.

By means of the apparatus 1 having the aforementioned configuration, carbon nanowalls can be produced through, for example, the following procedure. Specifically, the base 5 is placed on the second electrode 24, and a gaseous raw material substance (raw material gas) 32 and oxygen gas 33 are supplied through the raw material inlet 12 and the oxygen inlet 13, respectively, into the reaction chamber 10 at specific feed rates. A gaseous radical source substance (radical source gas)

36 is supplied through a radical source inlet 42 into the plasma formation chamber 46 at a specific feed rate. The vacuum pump (not illustrated) connected to the discharge outlet 16 is operated so that the pressure in the reaction chamber 10 (i.e., the total pressure of the partial pressure of the raw material gas, the partial pressure of oxygen gas, and the partial pressure of the radical source gas) is about 10 to about 2,000 mTorr. The preferred ratio of the feed rate of the raw material gas to that of the radical source gas may vary with, for example, the types (compositions) of these gases, or the properties and characteristics of carbon nanowalls of interest. When, for example, a C1 to C3 fluorocarbon is employed as a raw material gas, and hydrogen gas is employed as a radical source gas, these gases may be supplied so that the ratio of the feed rate of the raw material gas to that of the radical source gas (e.g., the feed rate ratio when these gases are supplied at similar temperatures) is 2/98 to 60/40. The feed rate ratio is preferably 5/95 to 50/50, more preferably 10/90 to 30/70. The ratio of the feed rate of the oxygen gas to that of the raw material gas is preferably 1/100 to 2/10, more preferably 2/100 to 12/100.

Thus, a plasma of the raw material gas 32 and a plasma of the oxygen gas 33 are formed generally between the first electrode 22 and the second electrode 24, to thereby provide the plasma atmosphere 34. Microwaves (e.g., 2.45 GHz) are introduced into the waveguide 47 for decomposing the radical source gas 36 in the plasma formation chamber 46, to thereby generate the radicals 38. The thus-generated radicals 38 are introduced through the radical inlets 14 into the reaction chamber 10, and injected into the plasma atmosphere 34, whereby the raw material gas plasma forming the plasma atmosphere 34 is mixed with the radicals 38 supplied from outside the atmosphere. Thus, carbon nanowalls can be grown on the top surface of the substrate 5 placed on the second electrode 24. In this case, preferably, the temperature of the substrate 5 is maintained at about 100 to about 800° C. (more preferably, about 200 to about 600° C.) by means of, for example, the heater 25. next, a carbon nanostructure was formed on the substrate 5 by means of the aforementioned apparatus 1, to thereby fabricate a sample substrate for laser desorption ionization mass spectrometry. The characteristics of the thus—formed carbon nanostructure were evaluated. Specifically, $C_2F_6$ was employed as the raw material gas 32. Hydrogen gas ($H_2$) was employed as the radical source gas 36. A silicon (Si) substrate having a thickness of about 0.5 mm was employed as the substrate 5. The silicon substrate 5 contains substantially no catalyst (e.g., metal catalyst). The silicon substrate 5 was placed on the second electrode 24 so that the (100) plane of the substrate 5 faced the first electrode 22. The raw material gas 32 (i.e., $C_2F_6$) was supplied through the raw material inlet 12 into the reaction chamber 10; the oxygen gas 33 was supplied through the oxygen inlet 13; and the radical source gas 36 (i.e., hydrogen gas) was supplied through the radical source inlet 42. The reaction chamber 10 was evacuated through the discharge outlet 16.

$C_2F_6$ was supplied into the reaction chamber 10 at 50 sccm; hydrogen gas was supplied into the plasma formation chamber 46 at 100 sccm; and oxygen gas was supplied into the reaction chamber 10 at 0, 2, or 5 sccm. Evacuation conditions were controlled so that the total pressure was adjusted to about 1.2 Torr. While the raw material gas 32 and the oxygen gas 33 were supplied under the aforementioned conditions, an RF power (13.56 MHz, 100 W) was applied from the power supply to the first electrode 22, and RF waves were applied to the raw material gas 32 ($C_2F_6$) and the oxygen gas 33 contained in the reaction chamber 10. Thus, a plasma of the raw material gas 32 and a plasma of the oxygen gas 33 were formed, whereby the plasma atmosphere 34 was provided between the first electrode 22 and the second electrode 24.

While the radical source gas 36 was supplied under the aforementioned conditions, microwaves were introduced into the waveguide 47, and microwaves were applied to the radical source gas 36 ($H_2$) contained in the plasma formation chamber 46. The thus-generated H radicals were introduced through the radical inlets 14 into the reaction chamber 10. Thus, a carbon nanostructure was grown (formed) on the (100) plane of the silicon substrate 5. In the embodiment, the nanostructure was grown for 20 minutes (in the case of supply of no oxygen gas) or 40 minutes (in the case of supply of oxygen gas). During this growth period, the temperature of the substrate 5 was maintained at about 500° C. by using, as necessary, the heater 25 or a cooling apparatus (not illustrated).

Carbon nanowalls produced under the aforementioned conditions were observed under a scanning electron microscope (SEM). FIGS. 2(a) to 2(c) are SEM images of cross sections of carbon nanowalls produced through the aforementioned method, and FIGS. 2(d) to 2(f) are SEM images of the respective corresponding carbon nanowalls as viewed from above. FIGS. 2(a) and 2(d) are SEM images of carbon nanowalls corresponding to the case where no oxygen gas was supplied to the plasma atmosphere. FIGS. 2(b) and 2(e) are SEM images of carbon nanowalls corresponding to the case where oxygen gas was supplied at 2 sccm; i.e., the ratio of the feed rate of oxygen gas to the total feed rate (150 sccm) of $C_2F_6$ (50 sccm) and hydrogen gas (100 sccm) was 1.3%. FIGS. 2(c) and 2(f) are SEM images of carbon nanowalls corresponding to the case where oxygen gas was supplied at 5 sccm; i.e., the ratio of the feed rate of oxygen gas to the total feed rate (150 sccm) of $C_2F_6$ (50 sccm) and hydrogen gas (100 sccm) was 3.2%.

In the case where no oxygen gas was supplied, carbon nanowalls were grown at a rate of 60 nm/min, and the thus—grown carbon nanowalls had a height of 1,200 nm. However, as is clear from FIGS. 2(a) and 2(d), each carbon nanowall had numerous branches and did not extend smoothly.

In contrast, in the case where oxygen gas was supplied at 2 sccm, carbon nanowalls were grown at a rate of 19 nm/min., and the thus-grown carbon nanowalls had a height of 760 nm. As is clear from FIGS. 2(b) and 2(e), there were produced carbon nanowalls which had no branching and extended smoothly.

In the case where oxygen gas was supplied at 5 sccm, carbon nanowalls were grown at a rate of 22 nm/min., and the thus—grown carbon nanowalls had a height of 890 nm. As is clear from FIGS. 2(c) and 2(f), there were produced carbon nanowalls which had no branching and extended smoothly.

In the above-described production process, $C_2F_6$ was employed as a raw material gas. However, since carbon nanowalls of high quality are formed through addition of oxygen plasma (formed through introduction of oxygen gas) to a plasma atmosphere containing carbon and fluorine in the presence of hydrogen radicals, the raw material gas may be another CF-based gas (e.g., fluorocarbon (C and F) such as $CF_4$ or fluorohydrocarbon (C, F, and H) such as $CHF_3$). Since such a plasma atmosphere contains the same constituent elements as those in the case where hydrogen radicals are added to $C_2F_6$, oxygen plasma can be formed from oxygen gas supplied to the raw material gases forming the plasma atmosphere. The ratio of the feed rate of oxygen gas to that of a raw material gas may be about 0.5% (i.e., when a small amount of oxygen is present in a plasma atmosphere). When an excessively large amount of oxygen gas is supplied, the oxygen gas may inhibit crystal growth of carbon nanowalls from a raw material gas. Therefore, the maximum of the ratio of the flow rate of oxygen gas to that of a raw material gas is considered to be 5% to 10%. Conceivably, such a flow rate ratio may be applied to the case where a CF-based or CHF-based raw material gas other than $C_2F_6$ gas employed, since the resultant plasma atmosphere contains the same constituent elements as those in the case where $C_2F_6$ is employed.

Also, the effects of the present invention are obtained by the action of oxygen atoms. Therefore, a small amount of O radicals or OH radicals may be effectively employed, or a mixture of these radicals may be employed.

Through the above-described procedure, a sample substrate for laser desorption ionization mass spectrometry was fabricated. Carbon nanowalls preferably have hydrophilicity. Thus, the following hydrophilization treatment may be performed.

Specifically, an atmospheric plasma is generated, and the cross-section thereof normal to the flow direction in the light emission zone is adjusted to be smaller than the surface area of the sample substrate for laser desorption ionization mass spectrometry. A sample substrate for laser desorption ionization mass spectrometry is positioned in the light emission zone so as to be irradiated with the plasma beam. The sample substrate is irradiated with the atmospheric plasma incident beam in a direction normal to the substrate surface, while the beam axis of the irradiation area is fixed at a predetermined position in the light emission zone. The sample substrate is scanned so that the entire surface of the sample substrate is irradiated with the plasma beam. Thus, hydrophilization treatment is completed.

The plasma temperature may be adjusted to 100° C. or lower. The gas employed for generating plasma may be argon, nitrogen, oxygen, or a mixture of two or all three of these. In the case of the argon-oxygen mixture gas, the oxygen content is preferably 0.1% to 10%. The diameter (of a cross-section normal to the axis in the visible light emission zone) of the plasma beam is preferably 5 mm or less. The surface temperature of the sample substrate for laser desorption ionization mass spectrometry during the hydrophilization treatment is adjusted to 100° C. or lower, most preferably 70° C. or lower. Thus, the sample substrate is not damaged.

The position of the sample substrate for laser desorption ionization mass spectrometry with respect to the axis of the plasma beam correlates with hydrophilicity. That is, in the case where the sample substrate for laser desorption ionization mass spectrometry is placed in the visible light emission zone provided by the plasma beam, high hydrophilic effect can be attained. Thus, the hydrophilicity of the sample substrate for laser desorption ionization mass spectrometry whose surface has been irradiated with the plasma beam can be maintained at high level. Through adjusting the cross-section of the atmospheric plasma beam normal to the flow direction in the light emission zone to be smaller than the surface area of the sample substrate for laser desorption ionization mass spectrometry, the plasma can be stabilized, and the plasma density of the surface normal to the beam axis can be uniform. Through positioning a sample substrate for laser desorption ionization mass spectrometry in the light emission zone so as to be irradiated by the plasma beam; irradiating the sample substrate with the atmospheric plasma incident beam in a direction normal to the substrate surface, while the beam axis of the irradiation area is fixed at a predetermined position in the light emission zone; and scanning the sample substrate so that the entire surface of the sample substrate is irradiated with the plasma beam, high hydrophilicity can be imparted uniformly to the entire surface of the sample substrate for laser desorption ionization mass spectrometry.

The plasma generator is an apparatus for generating glow discharge plasma under atmospheric pressure by use of a three-phase or multi (3 or more)-phase AC power source. From the viewpoints of down-scaling of the atmospheric glow discharge plasma generator, generating uniform glow discharge plasma, etc., the frequency of the n-phase AC power source is preferably about 20 Hz to about 200 Hz. Thus, when a booster circuit which elevates the AC voltage to an appropriate level (e.g., kV order) is employed, a commercial power source (50 Hz or 60 Hz) may be incorporated into a power circuit of an atmospheric glow discharge plasma generator. Although argon (Ar) gas or similar gas is most suitable for the aforementioned plasma source gas, there may be employed other gases that are known to be generally employed in the formation of atmospheric glow discharge plasma, in accordance with the uses and the type of works. Examples of the plasma source gas include rare gases such as He and Ne, nitrogen, air, and oxygen.

In the hydrophilization treatment, an oxygen-atom-containing gas, which reacts with the sample substrate for laser desorption ionization mass spectrometry, may be additionally supplied to a tiny space between the electrodes. Examples of the material of the discharge electrodes which may be employed in the invention include stainless steel, molybdenum, tantalum, nickel, copper, tungsten, and alloys thereof.

Particularly in the case where dents or grooves for promoting electron capture action (hollow cathode discharge) are formed, the length (along the gas flow direction) of each of the discharge electrodes, defining the discharge gap, is preferably adjusted to about 1 to about 10 mm. When the length is less than 1 mm or more than 10 mm, stable electric discharge fails to be attained. The dents or grooves preferably have a width or depth of, for example, about 1 mm or less, more preferably about 0.5 mm. When the width or depth of the grooves is more than 1 mm, stable electric discharge fails to be attained. The dents for promoting electron capture may have a dot-like form. Furthermore, the dents or grooves may also have any shape such as a columnar shape, a hemispherical shape, a prismatic shape, or a pyramidal shape. Note that the hydrophilization treatment may be performed through a technique disclosed in Japanese Patent Application No. 2008-19267.

As described above, hydrophilization treatment of the surface of the sample substrate for laser desorption ionization mass spectrometry, on which carbon nanowalls are formed so as to stand therefrom and onto which a sample is applied, may be carried out through irradiating the surface with a plasma beam. In the hydrophilization treatment, the sample application area of the substrate may be divided lattice-wise into blocks, where the lattice area serves as a non-hydrophilized area and the remaining blocks serves as hydrophilized blocks. By use of such a sample substrate, different samples are separately and individually applied onto different hydrophilized blocks. Through analyzing such a sample substrate by means of a mass spectrometer, a plurality of samples can be simultaneously analyzed.

Before carrying out the aforementioned hydrophilization treatment, carbon nanowalls are formed on the base of the sample substrate, and the substrate is removed from the carbon nanowall production apparatus. This substrate is transferred to another plasma generator, where hydrophilization treatment is performed by irradiating the substrate with a plasma beam. However, in an alternative procedure, carbon nanowalls are grown in a carbon nanowall production apparatus, supplying of other raw material gases is stopped, and oxygen gas is supplied to generate plasma, whereby the surfaces of carbon nanowalls are hydrophilized. Through the alternative procedure, production of sample substrates can be facilitated.

Figure 2:
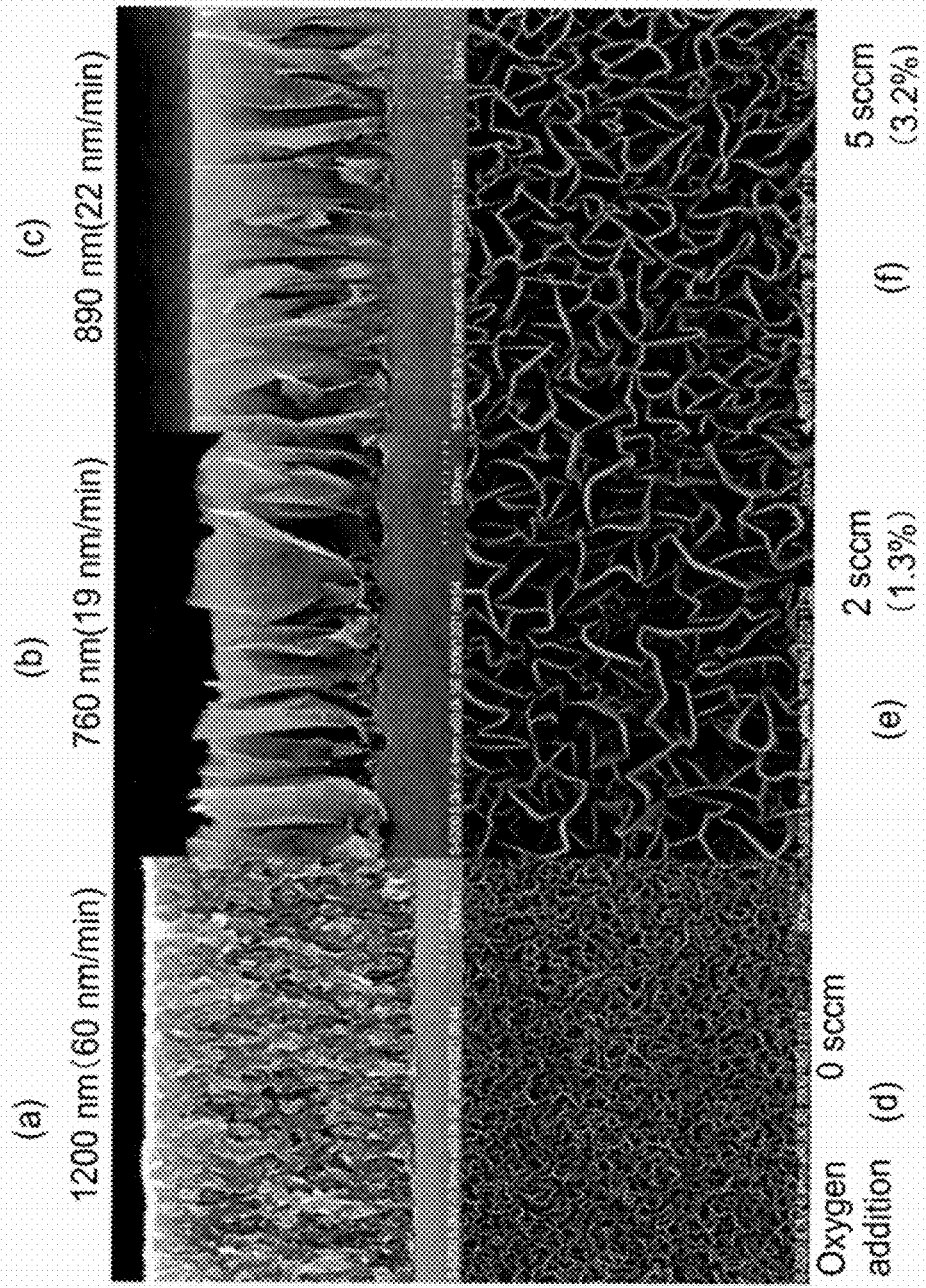

Then, when the surface of the sample substrate for laser desorption ionization mass spectrometry, on which carbon nanowalls are formed so as to stand therefrom, is irradiated with laser light by use of a nitrogen laser (wavelength: 337 nm) or Nd:YAG laser (wavelength: 266, 355, 532, or 1064 nm), carbon nanowalls absorb photoenergy of laser light having a specific wavelength. As a result, carbon nanowalls are rapidly heated, whereby sample molecules are conceivably ionized and dissociated from carbon nanowalls. Generally, in soft LDI-MS, a high voltage of about 20,000 V is applied to a sample substrate or sample substrate holder, virtually simultaneously with irradiation with laser light. Thus, conceivably, the ionized molecules are immediately released from the substrate via electrical repulsive force and are transferred into a mass separation section for mass spectrometric analysis. In other words, since sample molecules receive the energy required for ionization and dissociation not directly from laser light but indirectly from carbon nanowalls, soft ionization involving substantially no decomposition of molecules occurs, whereby the targeted high-sensitivity mass spectrometry can be attained. As shown in FIG. 2, carbon nanowalls have wall edges which are randomly undulated (as viewed from the top). The characteristic structure of carbon nanowalls effectively assists soft ionization of molecules.

In the present invention, the sample is prepared by dissolving a sample raw material in water or organic solvent. In the case of a bio-polymer (protein, peptide, or saccharide), the polymer is dissolved in a mixture of water containing 0.1 to 1% trifluoroacetic acid and acetonitrile (acetonitrile content: 5 to 75%), to thereby prepare a sample solution having a concentration of 1 to 100 pmol/μL. Depending of the solubility of the sample raw material, water or acetonitrile (100%) may be used as a solvent, or an organic solvent (e.g., methanol, ethanol, propanol, or acetone) may be used instead of acetonitrile. In the analysis of protein or peptide (i.e., the aforementioned bio-polymer), a proton-donating reagent such as citric acid or ammonium citrate may be added to a solvent in an amount of 0.1 to 5%, in addition to trifluoroacetic acid, in order to promote formation of stable ionic species via bonding of protons to sample molecules. In the analysis of saccharide (i.e., the aforementioned bio-polymer), a salt such as sodium chloride, potassium chloride, or sodium bromide may be added to a solvent so that the salt concentration is adjusted to 0.1 to 1 mg/mL, in order to form a stable ionic species of the sample via formation of alkali cation-adducts. In the case of the synthetic organic compound including synthetic organic polymer and oligomer, the organic compound is dissolved in an organic solvent capable of dissolving the compound, to thereby prepare a sample solution having a concentration of 0.1 to 1 mg/mL. No particular limitation is imposed on the organic solvent, so long as the solvent can dissolve the organic compound. Examples of the organic compound include chloroform, tetrahydrofuran, ethyl acetate, acetone, acetonitrile, propanol, ethanol, and methanol. A water-soluble synthetic polymer such as polyethylene glycol may be dissolved in water or a mixture of water and organic solvent. In order to form stable sample ions, a salt such as sodium chloride, potassium chloride, sodium bromide, silver trifluoroacetate, or silver nitrate may be added to a solvent so that the salt concentration is adjusted to 0.1 to 1 mg/mL. The aforementioned reagent concentrations are typical examples, and no particular limitation is imposed on the reagent concentration, so long as ions which can be analyzed through mass spectrometry can be formed.

Figure 3:
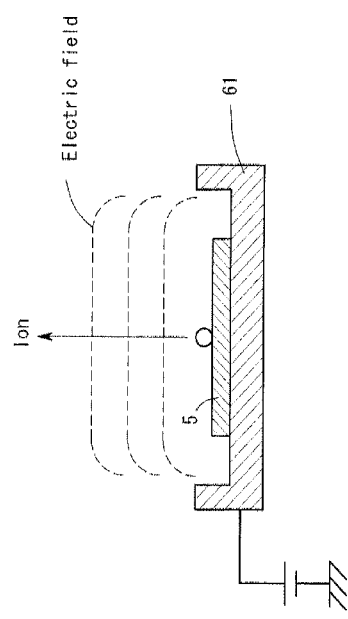
FIG. 3 A perspective view of the structure of a substrate for mass spectrometry according to the embodiment and a substrate holder.

Then, a sample solution (0.1 to 1 μL) is directly applied onto the sample substrate 5, which has been produced through the aforementioned method, and dried in air at room temperature, to thereby produce a uniform dried sample. A conductive sample substrate holder 61 shown in FIG. 3 serves as an electrode for accelerating ions placed in a mass spectrometer and employed for applying high voltage via a DC power source device 67. On the conductive sample substrate holder 61, the sample substrate 5 is placed while electrical conduction to the holder 61 is maintained. The conductive sample substrate 5 may be a metal sheet of conductive silicon, copper, stainless steel, etc. Alternatively, a sample substrate which is made of stainless steel and for use in LDI-MS may be employed as the conductive sample substrate 5. In this case, carbon nanowalls may be formed directly on the substrate holder 61 made of stainless steel. The material of the substrate holder 61 is not limited to the aforementioned materials, so long as the material is electrically conductive.

Figure 4:
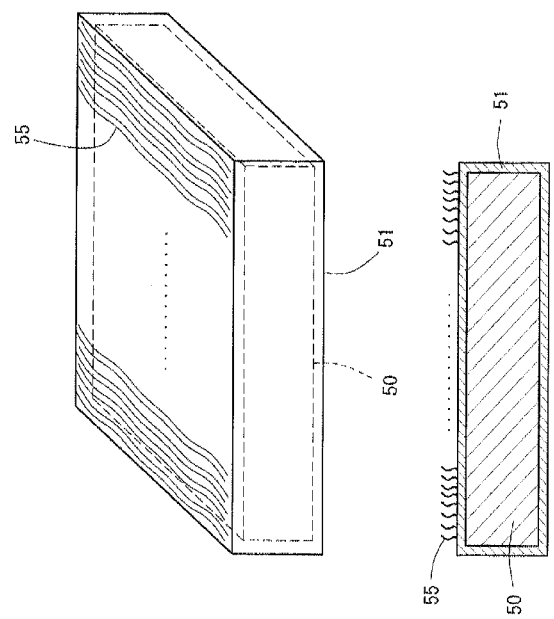
FIG. 4 A perspective view of the structure of another substrate for mass spectrometry according to the embodiment.

In the case where the sample substrate is produced from a ceramic material, glass, intrinsic silicon, or a similar material, each of the six faces of the sample substrate is coated with metallic film 51 through vapor deposition, to thereby provide a sample substrate 50. In this case, as shown in FIG. 4, carbon nanowalls 55 are formed on the metal film 51 which covers the substrate. Thus, the substrate 50 which is conductive to carbon nanowalls 55 is held by the substrate holder 61 which can be conductive to the substrate 50. The metal film 51 may be formed from, for example, Au, Al, or Ag. The metal thin film may be formed though a known technique such as film formation (e.g., vapor deposition or sputtering) or plating (e.g., electroless plating).

The substrate 50 to which conductivity has been imparted through the aforementioned procedure may be employed as a holder 61 which serves as an ion-acceleration electrode in a mass spectrometer. In this mode, the conductive sample substrate holder 61 shown in FIG. 3 does not have to be employed, whereby the mass spectrometer can be simplified. In addition, since a structural material such as double-sided tape is not needed, there can be prevented lowering of the degree of vacuum and contamination of the inside of the device, which would otherwise be caused by vaporized gas components released from the structural material in a high-vacuum ion source chamber, whereby mass spectrometry can be performed with higher precision.

Meanwhile, heat diffusion to the inside of the substrate is not preferred, in order to realize considerably high temperature in the vicinity of the laser radiation spot. Thus, the material of the sample substrate preferably has a low thermal conductivity.

The present invention will next be described in detail by way of Examples and Comparative Examples. However, the Examples are given only for the purpose of illustrating that the present invention is suited for analysis of a wide range of samples. Thus, the present invention is not limited to such analytes.

EXAMPLE 1

Application to Industrial Product (1)

A phenylenediamine anti-oxidant [4,4'-(α,α-dimethylbenzyl)diphenylamine] was dissolved in tetrahydrofuran (THF), to thereby prepare a 1-mg/mL sample solution. The sample solution (1 mL) was applied to a carbon nanowall element (i.e., a sample substrate containing carbon nanowalls formed on the surface so as to stand from the surface, the same applies to the following) and dried. The thus-treated element was affixed to a sample base for MALDI measurement, and the structure was placed in a time-of-flight type mass spectrometer (Voyager DE-PRO) equipped with an $N_2$ laser for analysis. The material of the substrate on which carbon nanowalls were formed was a conductive silicon substrate. The substrate assumed the shape of a square (10 mm×10 mm). The same substrate was also employed in the following Examples. However, needless to say, when there is employed a substrate made of a material other than silicon (e.g., an insulating silicon substrate, a conducting or insulating semiconductor substrate, a glass substrate, a ceramic substrate, a copper substrate, a stainless steel substrate, or a substrate made of another metal carbon) on which carbon nanowalls have been formed, high-precision measurement can also be performed.

Figure 5:
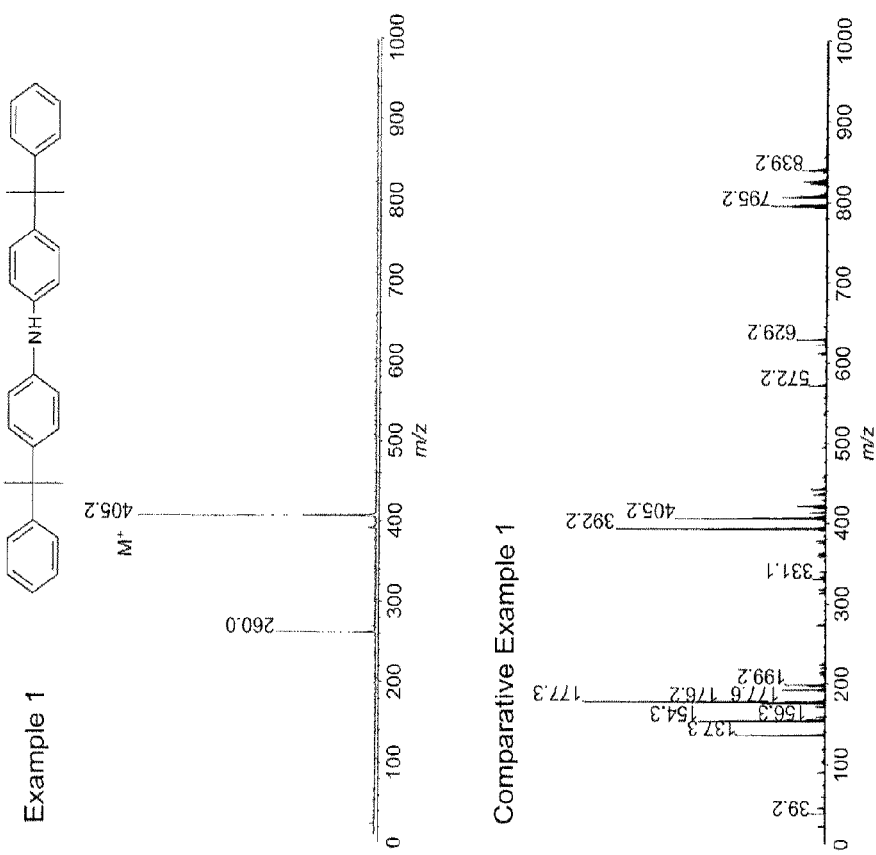
FIG. 5 Mass spectra of 4,4'-(α,α-dimethylbenzyl) diphenylamine measured in Example 1 and Comparative Example 1.

A mass spectrum of the anti-oxidant sample observed by use of the carbon nanowall element is shown in FIG. 5. $M^+$ ion of the anti-oxidant sample was clearly observed at an m/z of 405.2. As is clear from the spectrum, the anti-oxidant sample was found to be suitably analyzed through mass spectrometry employing the carbon nanowall element as an ionization device.

COMPARATIVE EXAMPLE 1

By use of 2,5-dihydroxybenzoic acid (DHB) as a matrix agent, MALDI-TOFMS of a phenylenediamine anti-oxidant [4,4'-($\alpha,\alpha$-dimethylbenzyl)diphenylamine] was performed. Specifically, the matrix was dissolved in tetrahydrofuran, to thereby prepare a 10-mg/mL matrix agent solution. The same sample solution as prepared in Example 1 was employed. The matrix agent solution, sample solution, and a cationizing agent were mixed at proportion of 5/1/1, and the resultant solution (1 mL) was applied to a sample base for MALDI and dried. The sample substrate was placed in a time-of-flight type mass spectrometer (Voyager DE-PRO) equipped with an $N_2$ laser for analysis. The obtained mass spectrum is also shown in FIG. 1. In Comparative Example 1, no carbon nanowall element was employed in a sample substrate.

In Comparative Example 1, MALDI-TOFMS was performed by use of DHB as a matrix agent. Since a number of peaks were observed, these peaks could not identified. Actually, a peak was observed at an m/z of 405.2, which was attributed to the sample. However, this identification was possible, since the mass of the sample was known. Therefore, the method of Comparative Example 1 is not suited for analysis of an unknown sample. In MALDI-TOFMS, various fragment peaks attributed to the matrix agent, and cluster ions of the fragments were generated. As is clear from Example 1 and Comparative Example 1, the above problem can be solved by the sample substrate of the present invention employing a carbon nanowall element and no matrix agent.

EXAMPLE 2

Application to Industrial Product (2)

A hindered phenol anti-oxidant (Irganox 1035, registered trademark) was dissolved in chloroform containing sodium iodide in a concentration of 0.5 mg/mL, to thereby prepare a 0.5-mg/mL sample solution. The sample solution (1 mL) was applied to a carbon nanowall element and dried. The thus-treated element was affixed to a sample base for MALDI measurement, and the structure was placed in a time-of-flight type mass spectrometer (Voyager DE-PRO) equipped with an $N_2$ laser for analysis.

Figure 6:
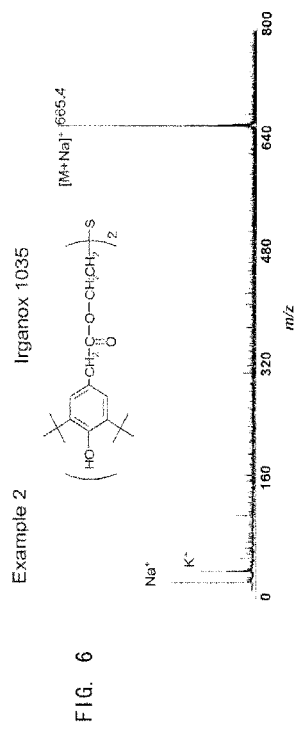
FIG. 6 A mass spectrum of Irganox 1035 measured in Example 2.

A mass spectrum of the anti-oxidant sample observed by use of the carbon nanowall element is shown in FIG. 6. [M+Na]$^+$ ion of the anti-oxidant sample was clearly observed at an m/z of 665.4. As is clear from the spectrum, the anti-oxidant sample was found to be suitably analyzed through mass spectrometry employing the carbon nanowall element as an ionization device.

EXAMPLE 3

Application to Industrial Product (3)

A polyoxyethylene nonionic surfactant (Triton X-100, registered trademark) was dissolved in chloroform containing sodium iodide in a concentration of 0.5 mg/mL, to thereby prepare a 0.5-mg/mL sample solution. The sample solution (1 mL) was applied to a carbon nanowall element and dried. The thus-treated element was affixed to a sample base for MALDI measurement, and the structure was placed in a time-of-flight type mass spectrometer (Voyager DE-PRO) equipped with an $N_2$ laser for analysis. Note that the surfactant is represented by $C_8H_{17}$—PhO—$(CH_2$—$CH_2$—$O)_n$—H (wherein Ph represents a phenyl group, and n is the number of repeating units).

Figure 7:
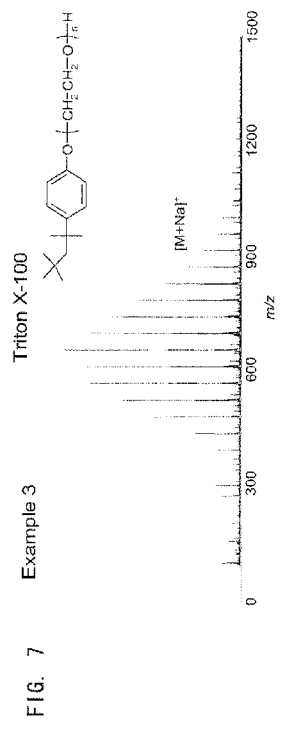
FIG. 7 A mass spectrum of Triton X-100 measured in Example 3.

A mass spectrum of the surfactant sample observed by use of the carbon nanowall element is shown in FIG. 7. [M+Na]$^+$ ion of the surfactant sample was clearly observed at a peak m/z of 650 or thereabout within a range of 400 to 1,200. Notably, peaks observed with intervals of mass of 44 are attributed to polyoxyethylene chain repeated units (—$CH_2$—$CH_2$—O—, mass of 44). The observed molecular distribution profile coincides with a report that a peak in the distribution profile is present in an n value range of about 3 to about 18 (G. A. Cumme, E. Blume, R. Bublitz, H. Hoppe, A. Horn, Journal of Chromatography A, 791, 245-253 (1997)). As is clear from the spectrum, a sample having a molecular weight range was found to be suitably analyzed through mass spectrometry employing the carbon nanowall element as an ionization device.

Aqueous samples were also tested. As a result, such samples were found to be ionized by means of a carbon nanowall element which has undergone hydrophilization. The following is an example case thereof.

EXAMPLE 4

Application to Peptide Sample Analysis

A peptide sample (angiotensin-I, monoiotope mass [M+H]$^+$ m/z of 1296.7) was dissolved in a methanol solution containing dihydrogen ammonium citrate, to thereby prepare a 1-pmol/μL sample solution. The sample solution (1 μL) was applied to a hydrophlized carbon nanowall element and dried. The thus-treated element was affixed to a sample base for MALDI measurement, and the structure was placed in a time-of-flight type mass spectrometer (AXIMA CFR-pulse) equipped with an $N_2$ laser for analysis.

Figure 8:
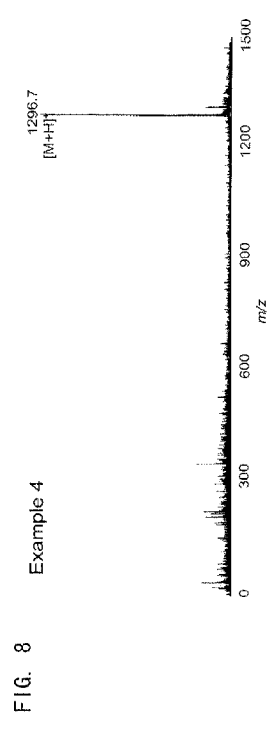
FIG. 8 A mass spectrum of angiotensin-I measured in Example 4.

FIG. 8 shows an observed mass spectrum of angiotensin-I. [M+H]$^+$ ion of angiotensin-I was clearly observed at an m/z of 1296.7. As is clear from the spectrum, a peptide sample was found to be suitably analyzed through employment of the hydrophlized carbon nanowall element as an ionization device.

EXAMPLE 5

Application to Protein Sample Analysis

A protein sample (myoglobin, molecular weight of 16951.5) was dissolved in a methanol solution containing dihydrogen ammonium citrate, to thereby prepare a 10-pmol/μL, sample solution. The sample solution (1 μL) was applied to a hydrophlized carbon nanowall element and dried. The thus-treated element was affixed to a sample base for MALDI measurement, and the structure was placed in a time-of-flight type mass spectrometer (AXIMA CFR-pulse) equipped with an $N_2$ laser for analysis.

Figure 9:
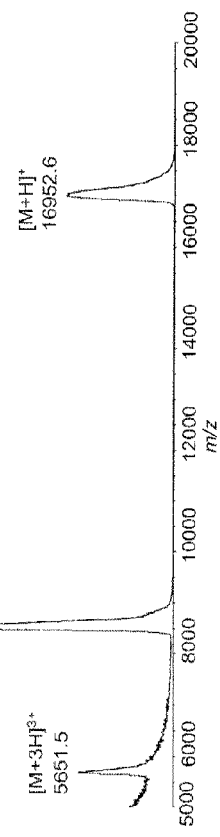
FIG. 9 A mass spectrum of myoglobin measured in Example 5.

FIG. 9 shows an observed mass spectrum of myoglobin. As is clear from the spectrum, a monovalent ion ($[M_+H]^+$) of myoglobin was observed at an m/z of 16952.6, a divalent ion ($[M2+H]^{2+}$) thereof was observed at an m/z of 8476.8, and a trivalent ion ($[M3+H]^{3+}$) thereof was observed at an m/z of 5651.5. It is well known that in ionization of protein through a soft ionization technique (e.g., matrix-assisted laser desorption ionization mass spectrometry), not only monovalent ion but also multivalent ions are prone to be generated. Thus, as is clear from Example 5, a protein sample was found to be suitably analyzed through employment of the hydrophlized carbon nanowall element as an ionization device.

EXAMPLE 6

Application to Saccharide Sample Analysis

β-Cyclodextrin (Wako Pure Chemical Industries, Ltd.) was dissolved in pure water, to thereby prepare a 1-mg/mL sample solution. The sample solution (1 μL) was applied to a hydrophlized carbon nanowall element and dried. The thus-treated element was affixed to a sample base for MALDI measurement, and the structure was placed in a time-of-flight type mass spectrometer (AXIMA CFR-pulse) equipped with an $N_2$ laser for analysis.

Figure 10:
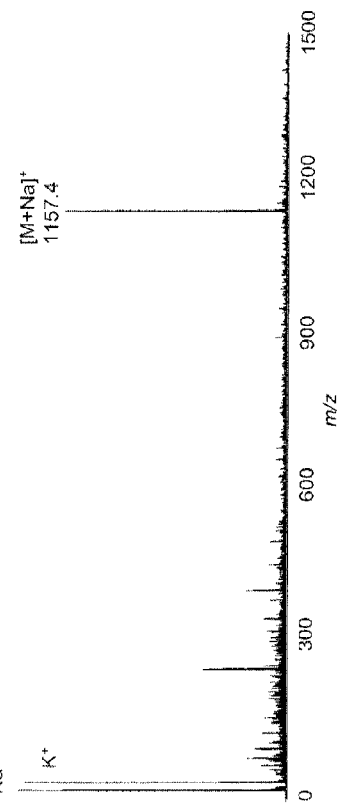
FIG. 10 A mass spectrum of P-cyclodextrin measured in Example 6.

FIG. 10 shows a mass spectrum of β-cyclodextrin observed by use of a sample substrate for laser desorption ionization mass spectrometry on which carbon nanowalls are formed so as to stand from the surface of the substrate. $[M+Na]^+$ ion of P-cyclodextrin was clearly observed at an m/z of 1157.4. Thus, as is clear from the spectrum, a saccharide sample was found to be suitably analyzed through employment of the hydrophlized carbon nanowall element as an ionization device.

[Conclusion]

As is clear from the Examples, when a substrate on which carbon nanowalls are formed so as to stand from the substrate was used as a sample substrate for laser desorption ionization mass spectrometry, only a few peaks other than those attributed to the target sample were observed in the observed spectrum. That is, noise was sufficiently avoided.

In contrast, a laser desorption ionization mass spectrometry employing a matrix requires an ionization-assisting agent which absorbs laser light energy to promote soft ionization of molecules. The spectrum of the ionization-assisting agent overlaps that of the sample, to thereby increase noise. In other words, in conventional methods, the spectral pattern of a soft ionization-assisting substance adapted to the analysis sample must be known in advance.

According to the present invention, no ionization-assisting agent is required to be added to the sample substance, since carbon nanowall promotes soft ionization of the sample substance. Thus, noise can be reduced in the observed spectrum. Therefore, according to the present invention, detection precision can be remarkably enhanced, and measurement can be carried out in a sample manner. Notably, no peak attributed to carbon atoms forming carbon nanowalls was observed in the obtained spectra. Thus, no decomposition or dissociation of carbon nanowalls occurred upon irradiation with laser light.

The present invention is particularly advantageous in mass spectrometry of a substance having a spectral pattern which nearly overlaps that of an ionization-assisting substance, which has conventionally been required. In other words, since the spectrum of the analyte does not overlap that of an ionization-assisting substance, even a low-molecular-weight sample can be correctly analyzed.

As is clear from the Examples, no limitation is imposed on the type of the sample to be analyzed, and various types of samples can be analyzed. Furthermore, the present invention enables mass spectrometry in a molecular weight range of low value to a value of 17,000. Since carbon nanowalls themselves promote soft ionization of molecules, samples having a molecular weight higher than the above upper limit may be analyzed by the present invention.

In the present invention, when the sample raw material is sold, the material is dissolved in a solvent (containing water) to prepare a sample solution. However, when the sample itself is liquid, the liquid may be used as is. Furthermore, if the sample can be directly applied to sidewalls of standing carbon nanowalls, the sample is not necessarily prepared to a solution.

Figure 11:
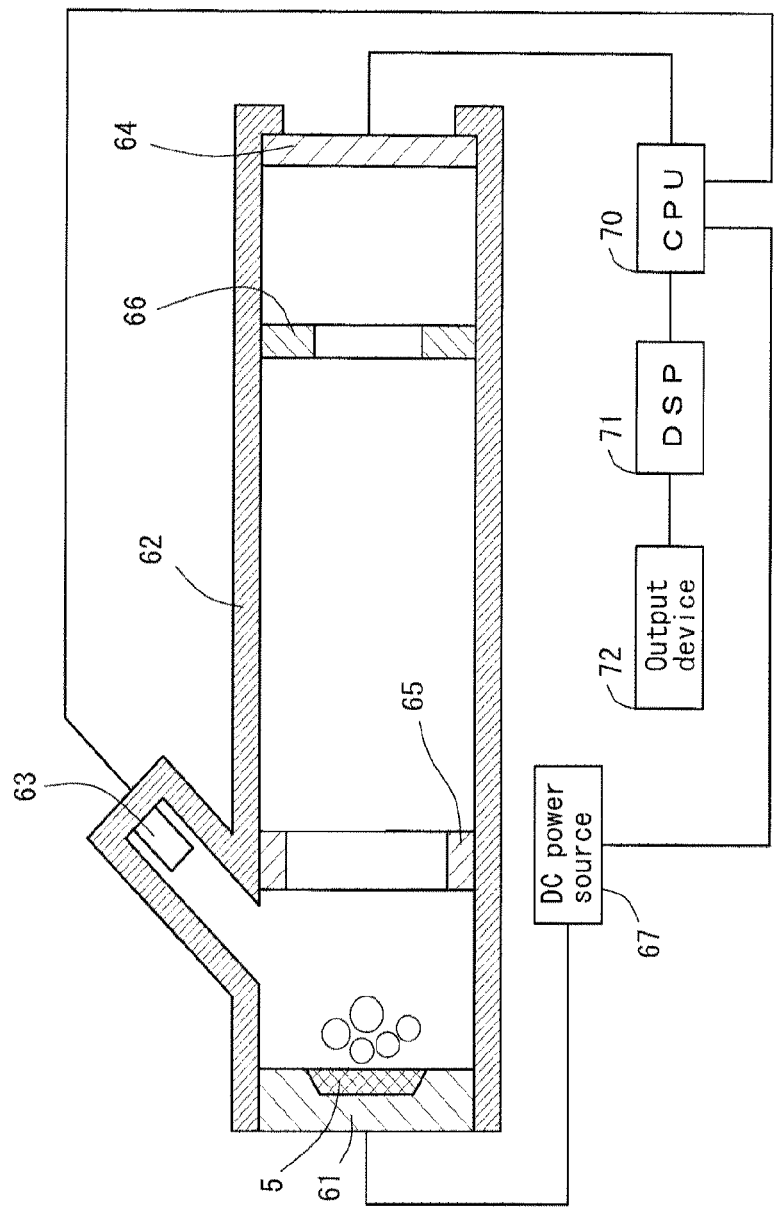
FIG. 11 The configuration of a laser desorption ionization mass spectrometer according to the embodiment of the present invention.

No particular limitation is imposed on the type of the laser desorption ionization mass spectrometer employing the sample substrate of the present invention, so long as the spectrometer (device) can ionize the sample to molecular fragments through laser light. FIG. 11 is a principle diagram of an embodiment of the device according to the present invention. The device has a casing 62 which can realize reduction of the inner pressure to vacuum. A sample holder 61 is disposed at one end face of the casing 62. A sample substrate 5, which has been produced through the aforementioned procedure, is formed on the sample holder 61. Over the sample substrate 5, a laser device 63 is disposed for irradiating the substrate with laser light. In the casing 62, an electrode 66 is disposed for accelerating molecular ions dissociated from the sample. By means of a DC power source 67, a voltage is applied between the sample holder 61 and the electrode 66. In the ion flight path, an electromagnetic field generator 65 is disposed. Separately, a field generator 67 is provided for controlling the ion flight path so that the flight path length is proportional to the mass (i.e., to attain constant resolution with respect to mass of molecular ion species). At the other end face of the casing 62, an ion detector 64 is disposed. As soon as the ion detector 64 detects coming ions, a detection signal is output to a CPU 70. The CPU 70 is a device which controls the timing of pulse laser output by the laser device 63 and the timing of voltage application by the DC power source 67 and which calculates times of flight of ions. The CPU 70 calculates the mass per unit charge from the time of flight obtained from the detection signal and outputs the results as a spectrum. The spectrum is displayed by a DSP 71, and the chart is printed by the output device 72.

The mass spectrometer of the invention basically has the above described structure. The sample substrate of the present invention may also be incorporated into other known commercial available mass spectrometers, which are somewhat modified devices of the above structure.

INDUSTRIAL APPLICABILITY

The present invention can be applied to mass spectrometry of molecules such as protein and polymer material.

The invention claimed is:

1. A sample substrate for laser desorption ionization mass spectrometry, the sample substrate comprising:
   a base and carbon nanowalls comprising wall surfaces onto which a sample to undergo mass spectrometry is applied,
   wherein the carbon nanowalls are formed on the base so as to stand on the base and comprise graphene sheets standing on the base, the carbon nanowalls extending two-dimensionally to have lengths in longitudinal and lateral directions which are greater than a thickness thereof.

2. A sample substrate for laser desorption ionization mass spectrometry according to claim 1, wherein the surfaces of the carbon nanowalls serve as a medium for ionization of the sample.

3. A sample substrate for laser desorption ionization mass spectrometry according to claim 1, wherein the surfaces of the carbon nanowalls have been hydrophilized.

4. A sample substrate for laser desorption ionization mass spectrometry according to claim 2, wherein the surfaces of the carbon nanowalls have been hydrophilized.

5. A method for performing laser desorption ionization mass spectrometry, the method comprising:
employing a sample substrate for laser desorption ionization mass spectrometry as recited in claim 1.

6. A method for performing laser desorption ionization mass spectrometry, the method comprising:
employing a sample substrate for laser desorption ionization mass spectrometry as recited in claim 2.

7. A method for performing laser desorption ionization mass spectrometry, the method comprising:
employing a sample substrate for laser desorption ionization mass spectrometry as recited in claim 3.

8. A device for performing laser desorption ionization mass spectrometry, characterized in that the device is configured to receive therein a sample substrate for laser desorption ionization mass spectrometry as recited in claim 1.

9. A device for performing laser desorption ionization mass spectrometry, characterized in that the device is configured to receive therein a sample substrate for laser desorption ionization mass spectrometry as recited in claim 2.

10. A device for performing laser desorption ionization mass spectrometry, characterized in that the device is configured to receive therein a sample substrate for laser desorption ionization mass spectrometry as recited in claim 3.

11. A sample for laser desorption ionization mass spectrometry, characterized in that the sample is produced by preparing a solution of a sample, applying the solution of the sample onto a sample substrate for laser desorption ionization mass spectrometry as recited in claim 1, and drying.

12. A sample for laser desorption ionization mass spectrometry, characterized in that the sample is produced by preparing a solution of a sample, applying the solution of the sample onto a sample substrate for laser desorption ionization mass spectrometry as recited in claim 2, and drying.

13. A sample for laser desorption ionization mass spectrometry, characterized in that the sample is produced by preparing a solution of a sample, applying the solution of the sample onto a sample substrate for laser desorption ionization mass spectrometry as recited in claim 3, and drying.

14. A sample substrate for laser desorption ionization mass spectrometry according to claim 1, wherein the carbon nanowalls have an aspect ratio defined as a height of a wall/a width of the wall, which is 200 or more.

15. A sample substrate for laser desorption ionization mass spectrometry according to claim 1, wherein the carbon nanowalls have no branching in a height direction.

16. A sample substrate for laser desorption ionization mass spectrometry according to claim 1, wherein carbon nanowalls comprise wall edges which are randomly undulated.

17. A sample substrate for laser desorption ionization mass spectrometry according to claim 1, wherein the carbon nanowalls are in a linear contact with the sample formed thereon.

18. A sample substrate for laser desorption ionization mass spectrometry according to claim 1, wherein the carbon nanowalls have a uniform in-plane density to stand from the sample substrate with nanometer-order spacing intervals.

* * * * *